(12) United States Patent
Mueller-Pathle

(10) Patent No.: US 11,660,400 B2
(45) Date of Patent: May 30, 2023

(54) SENSOR ARRANGEMENT FOR AN INJECTION DEVICE

(71) Applicant: SANOFI-AVENTIS DEUTSCHLAND GMBH, Frankfurt am Main (DE)

(72) Inventor: Stephan Mueller-Pathle, Frankfurt am Main (DE)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 577 days.

(21) Appl. No.: 16/728,072

(22) Filed: Dec. 27, 2019

(65) Prior Publication Data

US 2020/0222636 A1      Jul. 16, 2020

Related U.S. Application Data

(63) Continuation of application No. 15/555,853, filed as application No. PCT/EP2016/054324 on Mar. 1, 2016, now Pat. No. 10,518,040.

(30) Foreign Application Priority Data

Mar. 6, 2015    (EP) ..................................... 15158011

(51) Int. Cl.
*A61M 5/315*        (2006.01)
*G01R 33/038*       (2006.01)
(Continued)

(52) U.S. Cl.
CPC .......... *A61M 5/31568* (2013.01); *A61M 5/24* (2013.01); *A61M 5/2466* (2013.01);
(Continued)

(58) Field of Classification Search
CPC ............ A61M 5/31526; A61M 5/3158; A61M 5/31568; A61M 5/31541; A61M 5/31593;
(Continued)

(56) References Cited

U.S. PATENT DOCUMENTS

2006/0161112 A1*  7/2006  Steffen .................. G01D 5/145
                                                            604/188
2007/0000502 A1   1/2007  Chong et al.
(Continued)

FOREIGN PATENT DOCUMENTS

CN        1820181        8/2006
CN      104519931        4/2015
(Continued)

OTHER PUBLICATIONS

International Preliminary Report on Patentability in International Application No. PCT/EP2016/054324, dated Sep. 12, 2017, 7 pages.

(Continued)

*Primary Examiner* — Emily L Schmidt
*Assistant Examiner* — Alexandra Lalonde
(74) *Attorney, Agent, or Firm* — Fish & Richardson P.C.

(57) ABSTRACT

The disclosure relates to a sensor arrangement for an injection device to determine an axial position of at least one device component of the injection device inside a housing of the injection device. The sensor arrangement includes an elongated member located inside the housing, extending in an axial direction and having at least a first section and a second section of different magnetization. The first and second sections are separated in the axial direction. The sensor arrangement also includes at least one magnetic sensor element attached to the housing to detect the axial position of at least one of the first and second sections.

19 Claims, 3 Drawing Sheets

(51) Int. Cl.
*G01D 5/245* (2006.01)
*A61M 5/24* (2006.01)
*G01R 33/02* (2006.01)
*G01D 5/20* (2006.01)
*A61M 5/31* (2006.01)
*G01D 5/14* (2006.01)
*A61M 5/32* (2006.01)

(52) U.S. Cl.
CPC .... *A61M 5/31525* (2013.01); *A61M 5/31541* (2013.01); *A61M 5/31551* (2013.01); *A61M 5/31581* (2013.01); *G01D 5/2013* (2013.01); *G01D 5/2451* (2013.01); *G01R 33/02* (2013.01); *G01R 33/038* (2013.01); *A61M 5/31553* (2013.01); *A61M 5/31585* (2013.01); *A61M 5/31593* (2013.01); *A61M 5/3202* (2013.01); *A61M 2005/3126* (2013.01); *A61M 2205/0238* (2013.01); *A61M 2205/3317* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/8293* (2013.01); *G01D 5/145* (2013.01)

(58) Field of Classification Search
CPC .......... A61M 5/31525; A61M 5/31546; A61M 5/31533; A61M 5/31555; A61M 5/24; A61M 5/31528; A61M 5/31545; A61M 5/31548; A61M 5/31551; A61M 5/31581; A61M 5/31565; A61M 5/31585; A61M 5/3153; A61M 5/3155; A61M 5/3159; A61M 2005/3125; A61M 2005/3126; A61M 2005/3154; A61M 2205/3317; A61M 2205/6054; A61M 2205/0272; A61M 2205/33; A61M 2205/3379; G01R 33/02
See application file for complete search history.

(56) References Cited

U.S. PATENT DOCUMENTS

| | | | |
|---|---|---|---|
| 2007/0005021 A1 | 1/2007 | Kohlbrenner et al. | |
| 2008/0169307 A1 | 7/2008 | Hofstetter | |
| 2009/0137964 A1* | 5/2009 | Enggaard | A61M 5/178 604/207 |
| 2009/0264828 A1* | 10/2009 | Dette | A61M 5/31565 604/211 |
| 2010/0152672 A1* | 6/2010 | Raab | A61M 5/3148 604/208 |
| 2011/0215797 A1 | 9/2011 | Steinich et al. | |
| 2012/0022458 A1 | 1/2012 | Oh et al. | |

FOREIGN PATENT DOCUMENTS

| | | | |
|---|---|---|---|
| EP | 2454558 | 5/2012 | |
| EP | 24544558 | 5/2012 | |
| JP | 2007-506469 | 3/2007 | |
| JP | 2014-531283 | 11/2014 | |
| JP | 2015-528318 | 9/2015 | |
| JP | 2016-514591 | 5/2016 | |
| JP | 2016-518184 | 6/2016 | |
| WO | WO 2004/078239 | 9/2004 | |
| WO | WO 2004/078240 | 9/2004 | |
| WO | WO 2004/078241 | 9/2004 | |
| WO | WO 2011/006515 | 1/2011 | |
| WO | WO 2013/050535 | 4/2013 | |
| WO | WO 2014/023763 | 2/2014 | |
| WO | WO-2014023763 A1 * | 2/2014 | .......... A61B 5/4836 |
| WO | WO 2014/166894 | 10/2014 | |
| WO | WO 2014/166897 | 10/2014 | |

OTHER PUBLICATIONS

International Search Report and Written Opinion in International Application No. PCT/EP2016/054324, dated May 2, 2016, 11 pages.

* cited by examiner

SENSOR ARRANGEMENT FOR AN INJECTION DEVICE

CROSS SECTION TO RELATED APPLICATIONS

The present application is a continuation of U.S. patent application Ser. No. 15/555,853, filed on Sep. 5, 2017, which is the national stage entry of International Patent Application No. PCT/EP2016/054324, filed on Mar. 1, 2016, and claims priority to Application No. EP 15158011.5, filed in on Mar. 6, 2015, the disclosures of which are expressly incorporated herein in entirety by reference thereto.

TECHNICAL FIELD

The disclosure relates to an apparatus and method for recording the amount of medicament ejected from an injection device.

BACKGROUND

A variety of diseases exist which require regular treatment by injection of a medicament. Such injection can be performed by either medical personnel or by patients themselves. As an example, type-1 and type-2 diabetes can be treated by patients themselves by injection of insulin doses once or several times per day. It is known to couple a supplemental device to an insulin injection device for recording information about the doses which are administered. Supplemental devices may be used to record dose history information such as the various times at which insulin is administered and the quantity of insulin administered at each such time.

Although electronically recording dose history information addresses the problem of inaccurately recording such information manually, it has the disadvantage of providing a false representation of how much medicament a patient actually injects themselves with. In particular, before administering an injection a patient may eject a small amount of medicament in a so-called prime shot to remove air from within the needle. Supplemental devices configured to record how much medicament is ejected from an injection device may be operable to record both amounts of medicament ejected during prime shots in addition to amounts of medicament that are actually injected into a patient. It will thus be appreciated that simply recording how much medicament is ejected from an injection device does not give an accurate determination of how much medicament is actually injected into a patient. Not knowing such information within an acceptable degree of tolerance may have potentially serious consequences if a patient is subsequently over or under prescribed medication on the basis of an incorrect understanding of how much medicament has previously been injected.

Injection devices such like pen-type injectors also typically comprise a last dose limiting mechanism in order to prevent setting of a dose that would exceed the amount of medicament left in a cartridge. Such last dose limiting mechanisms are typically mechanically implemented, for instance by a last dose limiting member threadedly engaged with a sleeve or rod that is exclusively rotatable during a dose setting procedure but which is rotationally fixed and in non-rotative engagement with a housing of a device during dose dispensing or dose delivery. In addition to gather information about the total amount of medicament injected into a patient it is desirable to obtain precise information about a residual filling level of a cartridge actually in use. Especially when a supplemental device is equipped with a display, information about the quantity and amount of medicament left in a cartridge could be visually displayed or audibly communicated to a user.

Gathering of information related to the actual device status, such like information about a total amount of medicament delivered or a residual amount of medicament left in a cartridge is quite tricky and elaborate when the delivery device is implemented all mechanically and when the supplemental device should be detachably connectable to the injection device.

SUMMARY

The disclosure relates to a sensor arrangement for an injection device, and in particular to a sensor arrangement capable to determine the axial position of at least one component of the injection device. In another aspect the disclosure relates to a supplemental device attachable to or connectable with an injection device and being operable to determine an amount of a medicament left in a cartridge and/or to determine an amount of a medicament already dispensed and/or delivery by the injection device.

A first aspect relates to a sensor arrangement for an injection device to determine an axial position of at least one component of the injection device, which device component is located inside the housing of the injection device. Typically, the at least one device component is axially displaceable relative to the housing of the injection device, wherein the actual axial position thereof is indicative of the total amount of medicament already dispensed or delivered and/or of a residual amount of medicament left in the cartridge. The sensor arrangement comprises an elongated member that is located inside the housing and which extends in an axial direction. Typically, the housing is also of elongated shape and also extends in axial direction.

The elongated member has at least a first section and at least a second section, wherein first and second sections exhibit different magnetization. Moreover, first and second sections are separated in axial direction in a non-overlapping way. They may be located at a particular axial distance and/or they may be located directly adjacently in axial direction. The sensor arrangement further has at least one magnetic sensor element attached to the housing and being operable to detect the axial position of at least one of the first and second sections, typically in regard to the housing. The magnetic field generated by first and second sections of different magnetization is characteristic.

Typically, first and second sections are permanently magnetized. A magnetic field vector of the magnetic field generated by the first section points in a direction different to the direction of a second magnetic field vector of the magnetic field generated by the second section. By having at least two sections of different magnetization along the elongated member the axial position of first and/or second sections relative to the at least one magnetic sensor element can be determined rather easily and with high precision. The magnetic fields of first and second sections of the elongated member may not only differ with regard to their directions but also with regard to their magnitude or strength. In this way, the elongated member may not only be magnetically encoded in axial direction with regard to a direction of various magnetic field sections but also with regard to a varying magnetic field strength.

By having at least a first and a second section of different magnetization along the elongated member, a spatial resolution of the sensor arrangement and its position determination capability can be improved. The axial size or axial extension of first and second sections may be directly correlated to a required resolution of the sensor arrangement. This could be of particular use to monitor and to detect an axial movement or axial displacement of the elongated member relative to the housing, typically during dose dispensing or dose delivery. The alternating and different magnetic fields of at least first and second sections of the elongated member are rather easily detectible by the at least one magnetic sensor as the elongated member is axially displaced relative to the housing and hence relative to the at least one magnetic sensor element.

The axial magnetic encoding of the elongated member is beneficial for a determination or measurement of an actual axial position of the elongated member, hence when the elongated member is stationary with regard to the housing. In another aspect the axially magnetically encoded elongated member is beneficial to precisely follow an axial displacement thereof relative to the housing by making use of a limited number of magnetic sensor elements. In principle, the sensor arrangement is already operable to determine the actual axial position of the elongated member and/or an axial displacement of the elongated member relative to the housing on the basis of a single magnetic sensor element.

According to a further embodiment the elongated member comprises a helical pattern of differently magnetized sections. Typically, the magnetization of axially adjacent sections of the elongated member changes according to a predefined offset angle. It is conceivable, that the elongated member comprises a sequence of at least four sections of different magnetization. A first magnetized section may exhibit a magnetic field vector pointing in a direction of 0°, a second section of the elongated member axially adjacent to the first section may have a magnetization vector pointing at 90°. A third section of the elongated member adjacent to the second section may have a magnetization with a magnetic field vector pointing in a direction of 180° and a fourth section of the elongated member axially adjacent to the third section may exhibit a magnetization with a magnetic field vector pointing in a direction of 270°. A fifth section adjacent to the fourth section may be equally magnetized as the first section. The magnetic field vectors typically lie in a plane extending perpendicular to the elongation of the elongated member.

It is generally conceivable, that the offset of the direction of magnetic field vectors of axially adjacently located sections of the elongated member is substantially constant along the elongated member. Alternatively it is even conceivable, that the directional offset of magnetic field vectors of magnetized section arranged axially adjacent along the elongated member changes over the elongation of the elongated member. Moreover, the total number of sections of the elongated member with different magnetization is by no way limited to only two, three or four different magnetizations. It is generally conceivable, that the helical pattern of differently magnetized sections is comprised of more than four sections of different magnetization. There may be five, six, seven, eight, nine, ten, eleven, twelve or even more sections along the elongated member having different magnetization. Depending on the axial extension of the sections of different magnetization the spatial resolution of the sensor arrangement can be arbitrarily increased and universally configured.

According to another embodiment the sensor arrangement comprises a magnetic sensor array having multiple sensor elements that are arranged along the axial direction and which are typically separated in axial direction. The sensor array may comprise a series of individual sensor elements equidistantly separated in axial direction. By means of a series of individual sensor elements the magnetization of more than one section of the elongated member but a whole sequence of differently magnetized sections of the elongated member can be sensed and determined rather simultaneously.

According to a further embodiment the elongated member is comprised of a magnetized material. Further, the elongated member may only comprise a magnetized or permanently magnetizable material. Moreover, magnetic particles may be embedded or distributed across the bulk of the elongated member. The elongated member may be generally made of different materials. For instance, the elongated member may comprise an injection molded plastic material, which is doped, charged or enriched with a magnetized or magnetizable material.

Especially when embedding magnetizable or magnetized particles into an injection-molded plastic material almost any axially elongated component of the injection device may be configured as and may thus serve as the magnetically encoded elongated member of the sensor arrangement.

According to another embodiment the elongated member comprises a magnetized coating. Here, a conventional elongated component of the injection device may be simply provided with a magnetic coating. In this way, rather conventional mechanical and axially elongated components of the injection device could be retrofitted and equipped with a magnetized or magnetizable coating so as to act as the elongated member for the magnetic sensor arrangement.

According to another embodiment the elongated member coincides with the at least one device component whose axial position relative to the housing is representative for the total amount of medicament injected or dispensed or whose axial position is indicative of the residual amount of medicament left in a cartridge of the injection device. The sensor arrangement may be entirely integrated into the injection device. Alternatively, the sensor arrangement is provided as a supplemental device releasably attachable to the injection device. When the sensor arrangement is implemented and provided by a supplemental device the elongated member of the sensor arrangement typically belongs to the injection device, in particular to its drive mechanism. In order for the sensor arrangement to work it is then only necessary to have an injection device having at least one elongated member located therein, which elongated member has at least a first section and a second section of different magnetization and being further separated in axial direction.

According to a further embodiment, the elongated member is mechanically engaged with a second device component which is axially displaceable along the elongated member. Typically, the axial position of the second device component relative to at least one of the housing and the elongated member is directly indicative or representative of the total amount of medicament already dispensed and/or of the residual amount of medicament left in a cartridge of the injection device.

In one embodiment, the second device component is a last dose limiting member of a drive mechanism of the injection device. The axial position of the second device component relative to the elongated member and/or relative to the housing is thus a direct indication of the status of the injection device. Typically, the axial position of the second device component is directly measurable or detectable by the at least one magnetic sensor element of the sensor arrangement. The second device component has an influence on the magnetic field of the differently magnetized sections of the elongated member. The second device component may attenuate or amplify the magnetic field of the elongated member. The second device component may be magnetized itself to magnetically interact with the magnetic field of the elongated member. A magnetic interaction between the elongated member and the second device component mechanically engaged therewith may be directly detectable or measurable by the at least one magnetic sensor element.

It is also conceivable that the second device component is permanently magnetized and that the second device component mechanically and magnetically interacts with the elongated device component, so that the magnetic field of first and second device components mutually interact.

Such a magnetic interaction may even further improve the precision and the resolution of the sensor arrangement.

The axial extension of the second device component may be further adapted to the axial extension of at least one of first and second sections of the elongated member. For instance, the axial extension of the second device component is substantially equal to the axial extension of at least one of first and second sections of the elongated member. In this way, the axial position of the second device component on the elongated member is precisely determinable.

According to another embodiment the second device component is ferromagnetic or ferrimagnetic. With a ferromagnetic or ferrimagnetic second device component, the axial position of the second device component relative to the elongated member and/or relative to the housing of the injection device is precisely determinable. A ferromagnetic or ferrimagnetic second device component is clearly and distinctively detectable by the at least one magnetic sensor element. With a ferromagnetic or ferrimagnetic second device component, the magnitude of magnetic field modification induced by the second device component may be rather large. In this way, the sensitivity of the at least one magnetic sensor element can be decreased, thereby allowing to make use of rather simple and cost efficient magnetic sensor elements without any negative effects in regard to precision and/or spatial resolution.

In a further embodiment, the second device component is threadedly engaged with the elongated member and is further rotatably fixed to the housing. The second device component is furthermore slidably displaceable relative to the housing. In this embodiment, the second device component may be implemented as a last dose limiting member of a last dose limiting mechanism of the drive mechanism of the injection device. The second device component is then for instance, keyed to the housing or is in splined engagement with the housing. One of the second device and an inside facing sidewall portion of the housing comprises a radial recess engaged with a correspondingly-shaped radial protrusion of the other one of second device component and inner sidewall of the housing.

In this way, the second device is permanently and rotatably fixed to the housing. Hence, it cannot rotate relative to the housing but may slide axially relative to the housing. In combination with such a splined engagement, the second device component is threadedly engaged with the elongated member. For instance, the second device component comprises a nut or a sleeve axially intersected by the elongated member. Here, the second device component comprises an inner thread that is engaged with a correspondingly-shaped outer thread of the elongated member.

In a further embodiment, the elongated member is rotatable inside the housing of the injection device. Typically, the elongated member comprises a drive sleeve or a similar component of a mechanically implemented drive mechanism of the injection device, which drive sleeve is exclusively rotatable during a dose setting procedure while it is rotationally fixed to the housing during dose delivery or during dose dispensing. In this way, the second device component is subject to an axial displacement relative to the housing and/or relative to the elongated member exclusively during dose setting.

According to another embodiment, the second device component is threadedly engaged with the housing and is rotatably fixed to the elongated member. Furthermore, the second device component is slidably displaceable relative to the elongated member. In this alternative embodiment, the second device component is splined to the elongated member. It is permanently rotationally engaged or rotationally locked to the elongated member and rotates together with the elongated member as the elongated member is subject to a rotation relative to the housing. Due to its threaded engagement with the housing, typically with an inside facing sidewall portion of the housing, the second device component is subject to an axial displacement as the elongated member is rotated relative to the housing.

Similar as to the embodiment described above the second device component is subject to an axial displacement exclusively during dose setting.

According to another embodiment, the second device component is a last dose limiting member of a drive mechanism of the injection device. The last dose limiting member, hence the second device component is exclusively subject to an axial displacement relative to the elongated member and/or relative to the housing. When arriving at a last dose position the second device component, hence the last dose limiting member radially and/or axially engages with one of the housing or the rotatable elongated member so as to block a further rotation of the elongated member relative to the housing in a dose incrementing direction. By means of the sensor arrangement the axial position of the second device component is precisely detectable or determinable. In an embodiment wherein the sensor arrangement is integrated into the injection device the sensor arrangement may provide a last dose limiting functionality. It may generate an audible, visual or haptic signal to a user thereby indicating that a last dose limiting configuration has been reached.

According to another embodiment, the elongated member is one of a piston rod, a dose indicator or a drive sleeve of a drive mechanism of the injection device. When implemented as a piston rod the axial position of the piston rod is directly detectable, typically by a magnetic sensor array. Likewise the last dose limiting member also the piston rod itself, in particular its axial position relative to the housing, is directly indicative of the total amount of medicament already dispensed or delivered and/or of a residual amount of medicament left in the cartridge.

In an alternative embodiment, the elongated member is implemented as a dose indicator. A dose indicator is typically rotatable relative to the housing during dose dispensing. However, the dose indicator typically rotates in a dose incrementing direction during dose setting and further rotates in an opposite dose decrementing direction during dose injection or dose delivery. However, the sensor arrangement may easily distinguish between a dose incrementing motion and a dose decrementing motion of the dose indicator during dose setting and dose dispensing, respectively. The sensor arrangement and eventually a control electrically connected with the sensor arrangement, in particular with its at least one magnetic sensor element, may easily distinguish between dose setting and dose dispensing motions of the elongated member implemented as a dose indicator. In this way the sensor arrangement may be adapted to selectively monitor the dose setting motions of the dose indicator implemented as the elongated member according to the definition of the sensor arrangement.

According to another alternative embodiment, the elongated member is implemented as a drive sleeve of a drive mechanism of the injection device. The drive sleeve is typically exclusively rotatable and/or axially displaceable relative to the housing during a dose setting action. The drive sleeve may be threadedly engaged with the second device component, typically implemented as a last dose limiting member. In particular the drive sleeve and the last dose limiting member could be implemented in a way as described in documents WO 2004/078239A1, WO 2004/078240A2 or WO 2004/078241 A1 the entirety of which is incorporated herein by reference and describing the mutual interaction of a drive sleeve and a nut thereby providing a last dose limiting mechanism. According to the terminology of these documents, the elongated member may be implemented as the drive sleeve while the second device component may be represented by the nut.

According to a further embodiment the at least one sensor element or the sensor array is arranged in a sensor housing attached to the housing of the injection device. The sensor housing may be releasably or detachably attachable to the housing of the injection device. Due to the magnetic encoding of the elongated member it is not necessary to manually establish an electrical connection between the injection device and the sensor arrangement. In this embodiment with a separate sensor housing the sensor arrangement is particularly implemented as a supplemental device, which is generally usable with several or different injection devices. In this way, various injection devices could be retrofitted with a sensor arrangement. Moreover, a sensor arrangement, hence a supplemental device comprising such a sensor arrangement may be designed and implemented as a personalized device of a user or patient making frequent use of different or disposable injection devices. In the event that an injection device is intended to be discarded since a medicament provided therein has been used up the supplemental device may be simply attached, e.g. clipped or otherwise attached to another injection device.

An injection monitoring could then simply continue regardless of the injection device the user actually uses.

Another aspect also relates to an injection device for setting and injecting of a dose of a liquid medicament. The injection device comprises a housing to accommodate a cartridge filled with the medicament to be injected. The injection device further comprises a drive mechanism comprising a piston rod to operably engage with a piston of the cartridge. Moreover, the injection device comprises a sensor arrangement as described above, which sensor arrangement is either attached to the housing, typically at the outer circumference of the housing or which sensor arrangement is arranged or located inside the housing. The sensor arrangement may be provided by a supplemental device distributed separately and independently of the injection device, wherein the supplemental device is typically usable with several, e.g. even with a sequence of injection devices. In an alternative embodiment the sensor arrangement may be integrated into the injection device.

According to another embodiment, the injection device comprises a cartridge that is filled with the medicament. The injection device equipped or equipable with the sensor arrangement is threadedly provided with a cartridge located therein. The injection device may be hence implemented as a disposable injection device. In another embodiment, the injection device may be implemented as a reusable injection device.

In still another aspect the injection device comprises at least one elongated member that is located inside the housing of the injection device, which elongated member extends in an axial direction and which elongated member has at least a first section and a second section of different magnetization, wherein first and second sections are separated in axial direction. In other words, the injection device comprises at least one device component of elongated shape and having first and second axial sections that are differently magnetized. In this way, the injection device is configured to cooperate with a sensor arrangement as described above, which sensor arrangement is then implemented as a supplemental device.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the injection device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2) 25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group-Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL).

The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

An advantage of certain aspects may be that the sensor arrangement is rather easy and cost efficient to manufacture and/or the sensor arrangement provides a precise positional determination or positional measurement.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following, an embodiment of the display arrangement, the drive mechanism and the injection device is described in detail by making reference to the drawings, in which.

DETAILED DESCRIPTION

Figure 1:
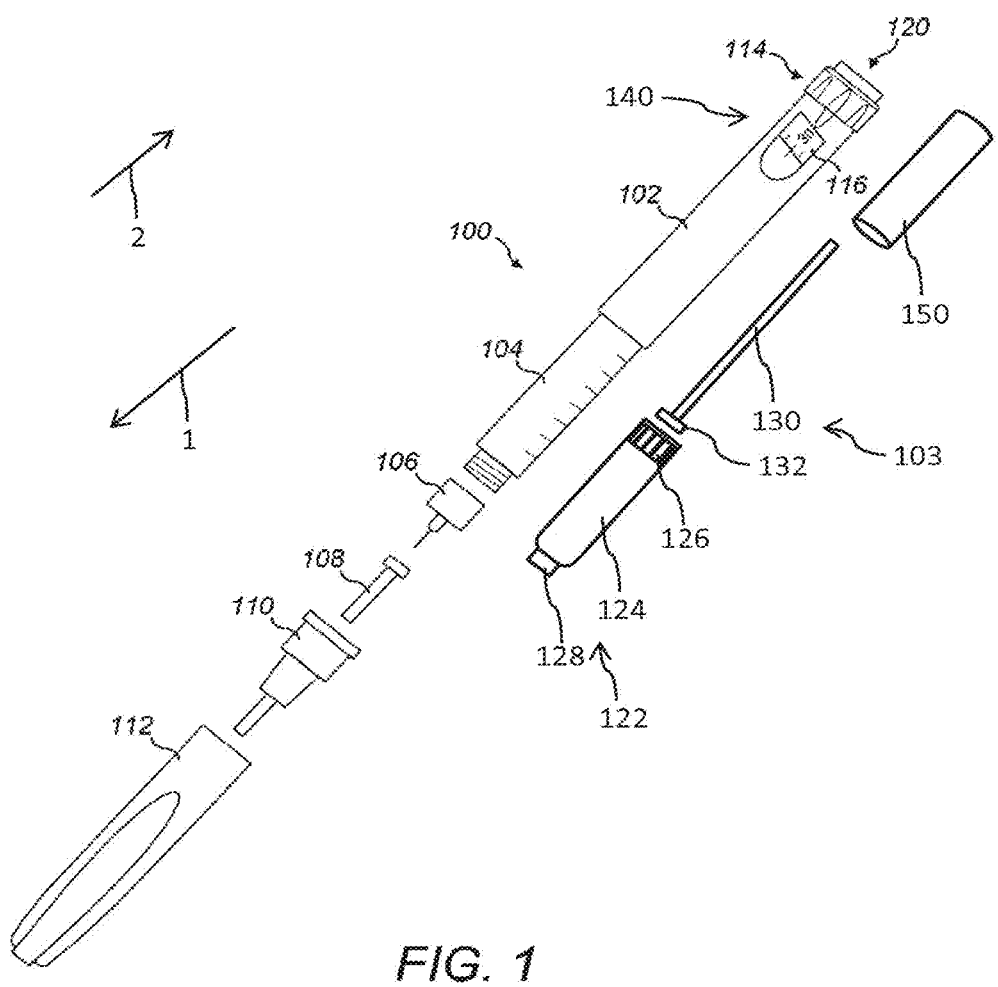
FIG. 1 schematically shows an injection device of pen-injector type.

In FIG. 1 an injection device 100 is schematically illustrated in an exploded view. The injection device 100 is of pen-injector type. It comprises an elongated housing 102, also denoted as body. The housing 102 is of elongated shape and extends in an axial distal direction 1 and opposite in an axial proximal direction 2. At its distal end the housing 102 is connected to a cartridge holder 104. The housing 102 as well as the cartridge holder 104 are of tubular shape. The cartridge holder 104 is configured to accommodate a cartridge 122 while the housing 102 is configured to accommodate a drive mechanism 103 comprising numerous mechanically interacting components by way of which a piston 126 of the cartridge 122 is displaceable in distal direction 1 in order to expel a medicament from the interior of the tubular-shaped barrel 124 of the cartridge 122.

The cartridge 122 further comprises a pierceable seal 128 at its distal end, which seal is penetrable or pierceable by a double-tipped injection needle of a needle assembly 106. As indicated in FIG. 1, the needle assembly 106 is releasably attachable to a distal end of the cartridge holder 104. As further shown in FIG. 1, the distal socket of the cartridge holder 104 comprises an outer thread to threadedly engage with a correspondingly-shaped inner thread of the needle assembly 106. The injection needle of the needle assembly 106 is initially covered with an inner needle cap 108. The entire needle assembly 106 is furthermore covered and equipped with an outer needle cap 110. Prior to conduct an injection procedure, outer and inner needle caps 110, 108 are to be detached from the needle assembly 106. The injection device 100 further comprises a protective cap 112 releasably attachable to the assembly of cartridge holder 104 and housing 102. Typically, the protective cap 112 covers the cartridge holder 104 while it is attached to the body 102.

The cartridge holder 104 is either of transparent material or comprises an inspection window to visually inspect the medicament located inside the barrel 124 of the cartridge 122. The cartridge 122, in particular its barrel 124 is typically made of a vitreous material, such like glass. The barrel 124 may be also made of a plastic material being substantially inert to the medicament located therein.

The drive mechanism 103 at least comprises a dose indicator 140 rotatably mounted inside the housing 102 and having numerous indicia or numbers printed on its outer circumference that are visible through a dosage window 116. The drive mechanism 103 further comprises a drive sleeve 150 operably engaged with the dose indicator 140 as well as with the piston rod 130. The piston rod 130 extending in axial direction comprises a radially widened pressure piece 132 at its distal end to exert distally directed pressure to the proximally facing portion of the piston 126 of the cartridge 120. In this way, a predefined amount of medicament, typically a dose of appropriate size is dispensable via the needle assembly 106 in fluid communication with the interior of the cartridge 122.

Furthermore, the drive mechanism 103 comprises a dose dial 114 that is rotatable in a dose incrementing direction and eventually also in a dose decrementing direction. Dialing of the dose dial 114 in either direction relative to the housing 102 allows a user to individually set and modify a dose of the medicament of required size. At the proximal end of the injection device 100 there is located an injection button 120. Depressing of the injection button 120, typically in distal direction 1 induces or triggers a dispensing action. During dispensing the dose indicator 140 typically returns into a zero dose configuration and the piston rod 130 drives in distal direction to displace the piston 126 further in distal direction for the purpose of dose dispensing. Generally, the drive mechanism 103 as shown here resembles or is even identical to the drive mechanism as disclosed in WO 2004/078239A1, WO 2004/078240A2 or WO 2004/078241 A1 the entirety of which is herein incorporated by reference.

Figure 5:
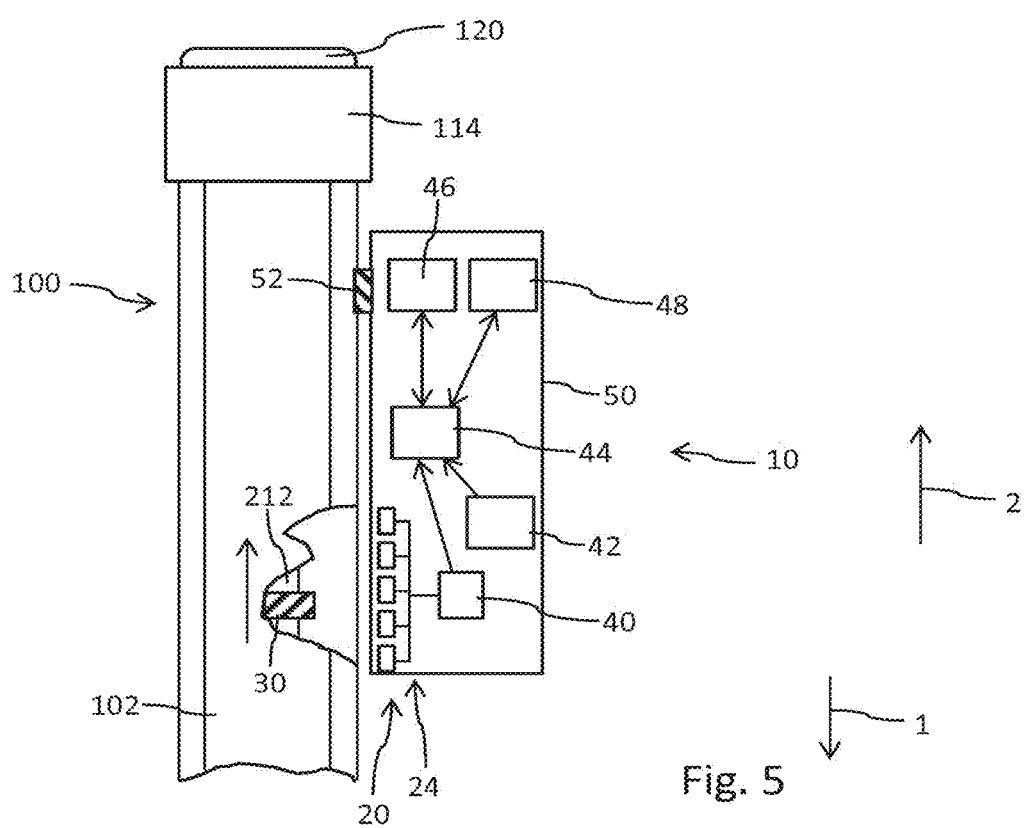

In FIG. 5 a sensor arrangement 10 to determine an axial position of at least one component of the injection device 100 is schematically illustrated. In this embodiment the sensor arrangement 10 is implemented as a supplemental device having a sensor housing 50 that is attached or which is generally attachable to the an outside facing sidewall portion of the housing 102 of the injection device 100. As indicated in FIG. 5, the sensor housing 50 is connected to the housing 102 by means of a fixation 52. In the embodiment as shown in FIG. 5 the sensor arrangement 10 comprises at least a magnetic sensor 20 having several sensor elements 22 arranged along the axial direction. Hence, the various sensor elements 22 are arranged side-by-side or adjacently in axial direction so as to form an axially elongated sensor array 24.

The sensor arrangement 10 typically comprises a sensor control 40 that is connected to all of the sensor elements 22. The sensor control 40 is operable to process the individual signals obtainable from the various sensor elements 22. The sensor control 40 is operable to provide an output to a processor 44 of the sensor arrangement 10, which processor 44 is operable to calculate an axial position of at least one device component 12, 212, and/or 30 of the injection device 100. Furthermore, the sensor arrangement 10 is equipped with a power supply, typically in form of an electric battery 42. Alternatively, the sensor arrangement 10 may be equipped with some other type of electrical power supply such like solar cells.

Moreover, the sensor arrangement 10 may be further equipped with a display 46 in order to visualize a particular status of the injection device 100. Additionally or alternatively, the sensor arrangement 10 comprises a communication unit 48 by way of which an axial position of the at least one device component determined by the processor 44 can be communicated to any further device. The communication unit 48 may provide wired or wireless data transmission to a further external device. The communication unit 48 may be provided with standard communication protocols, such like Bluetooth, RFID or other radio-frequency operated wireless transmission protocols.

Figure 2:
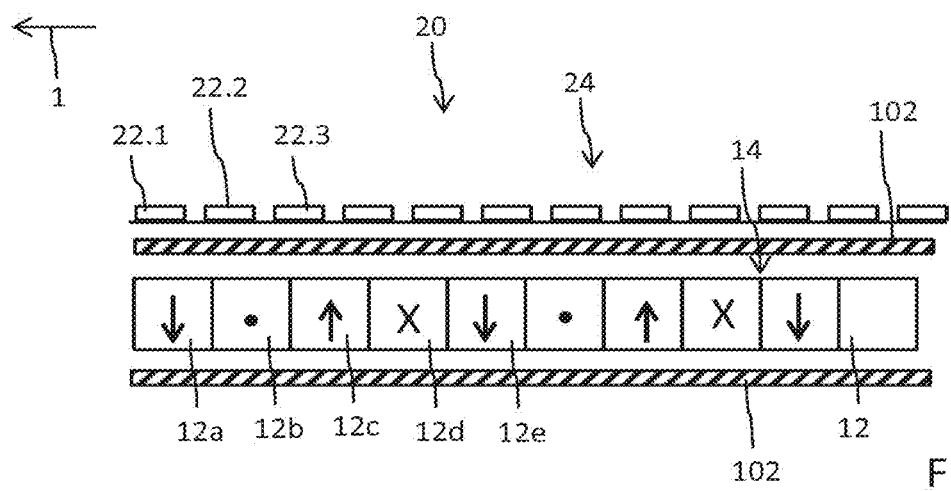
FIG. 2 shows a first embodiment of a sensor arrangement to determine an axial position of at least one device component.

In FIG. 2, a first embodiment of the sensor arrangement 10 is shown in greater detail. There, a longitudinal cross-section through the injection device 100 is provided. The sensor arrangement 10 comprises an elongated member 12 which elongated member 12 may be formed by the piston rod 130, by the dose indicator 140 or by the drive sleeve 150 of the drive mechanism 103 of the injection device 100. The elongated member 12 is axially displaceable inside the housing 102. As indicated in FIG. 2, the elongated member 12 is virtually divided into a number of sections 12a, 12b, 12c, 12d, 12e that are located axially adjacent. The sections 12a, 12b, 12c, 12d are of different magnetization as indicated by the arrows, points and crosses of the various sections 12a, 12b, 12c, 12d as shown in FIG. 2. In addition, the sensor arrangement 10 comprises at least one magnetic sensor element 22.1, 22.2, 22.3 only to mention a few. Typically the magnetic sensor 20 comprises a sensor array 24, formed by a longitudinal row of individual magnetic sensor elements 22.1, 22.2, 22.3 and so on. By means of the sensor array 24, the actual axial position of the elongated member 12 is precisely detectable. Moreover, also a movement of the elongated member 12 in axial direction 1 or 2 is directly detectable and quantitatively measurable by means of the sensor array 24.

Figure 4:
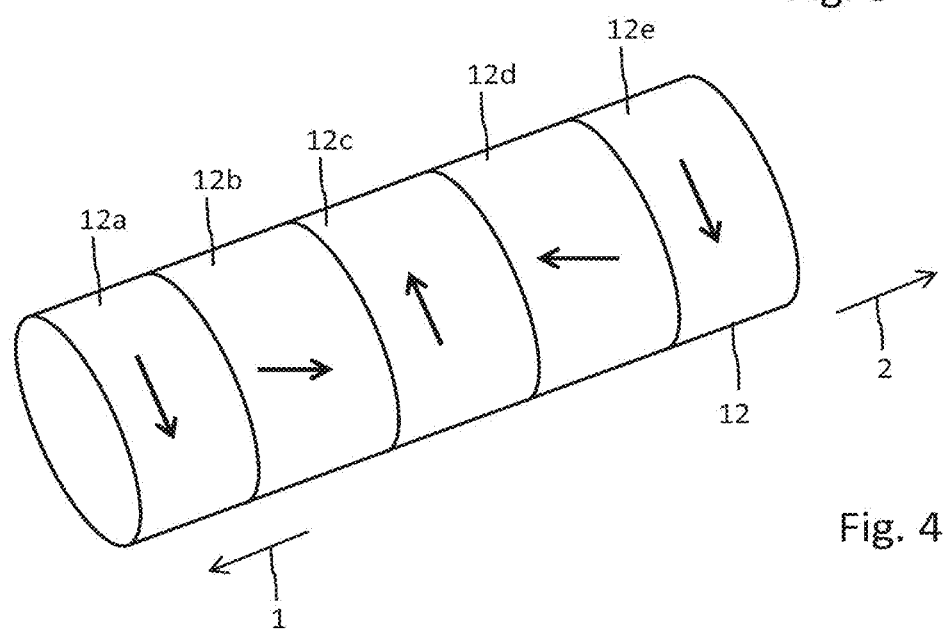

In FIG. 4, the different magnetizations of various sections 12a, 12b, 12c, 12d, 12e is shown in further detail. The elongated member 12 may be of substantially tubular elongated shape and the various sections 12a, 12b, 12c, 12d, 12e all extend over the entire cross-section of the elongated member in a plane substantially perpendicular to the axial elongation thereof. As shown in FIG. 4, the first section 12a has a magnetization pointing upwards. The second section 12b located axially adjacent to the first section 12a features a magnetization pointing to the right. A third section 12c adjacent to the second section 12b has a magnetization pointing downwards and a fourth section 12d axially adjacent to the third section 12c has a magnetization pointing substantially to the left. The fifth section 12e axially adjacent to the fourth section and has a magnetization pointing upwardly, like the first section 12a. In other words, the magnetization of adjacently arranged sections 12a, 12b, 12c, 12d, 12e of the elongated member 12 changes by a constant angle, presently by about 90°. The spiral or helical-shaped magnetization of the elongated member is similar to the one of a Halbach array. Moreover, the elongated member may be implemented as a Halbach array.

Figure 3:
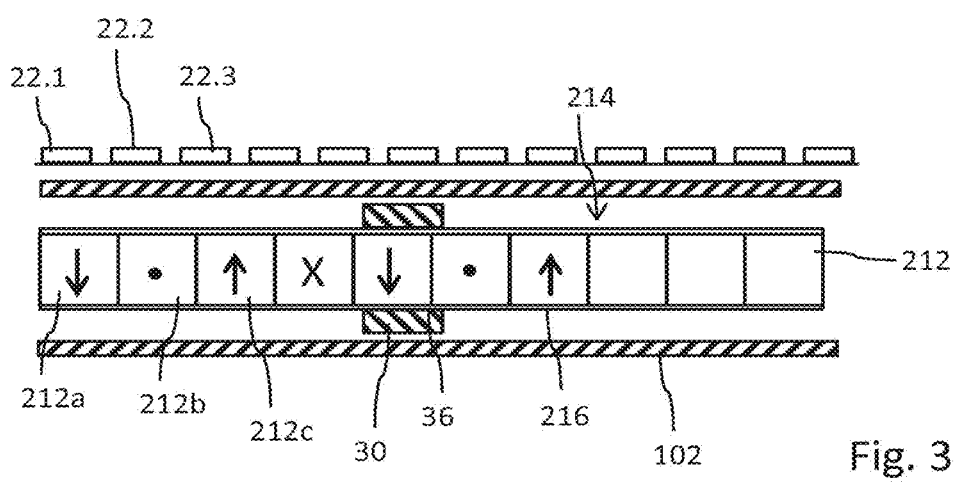
FIG. 3 shows another embodiment of the sensor arrangement, FIG. 4 schematically shows the elongated member with four axial sections of different magnetization and FIG. 5 schematically shows the sensor arrangement implemented as a supplemental device attached to the housing of the injection device.

In the embodiment according to FIG. 3 the sensor arrangement 10 comprises a slightly different elongated member 212. Also, this elongated member 212 may be implemented as one of a piston rod 130, a dose indicator 140 or a drive sleeve 150. The elongated member 212 is also segmented into various sections 212a, 212b, 212c, 212d, 212e and so on of different magnetization as indicated in FIG. 3. In contrast to the embodiment as described with respect to FIG. 2 the elongated member 212 as shown in FIG. 3 comprises an outer thread 216 by way of which the elongated member 212 is threadedly engaged with a second member 30. The second member 30 has an inner thread 36 and is hence axially displaceable relative to the elongated member through a rotation of the elongated member 212 relative to the second member 30.

Typically, the elongated member 212 is rotatable relative to the housing 102 while the second member 30 is rotationally locked to the housing 102 but is further axially displaceable relative to the housing 102. Typically, the second member 30 modifies the magnetic field of the elongated member 212. For this purpose the second member 30 may be ferromagnetic or ferrimagnetic. In this case, the present and the axial position of the second member 30 is easily detectable by the array of sensor elements 22.1, 22.2, 22.3. Alternative to a ferromagnetic or ferrimagnetic implementation of the second member it is also conceivable that the second member exhibits a paramagnetic or diamagnetic behavior that is detectable by the sensor array 24.

In order to obtain a predefined magnetized pattern of the elongated member, it is conceivable that the elongated member 12, 212 comprises a magnetized or magnetizable material in its bulk. Alternatively it is conceivable that the elongated member 12, 212 is provided with a magnetized or magnetizable coating 14, 214, which coating is magnetizable in axial sections in different directions.

LIST OF REFERENCE NUMBERS 1 distal direction
2 proximal direction
10 sensor arrangement
12 elongated member
12a,b,c,d,e section
14 coating
20 sensor
21.1 sensor element
22.2 sensor element
22.3 sensor element
24 sensor array
30 second member
36 thread
40 sensor control
42 power supply
44 processor
46 display
48 communication unit
50 sensor housing
52 fixation
100 injection device
102 housing
103 drive mechanism
104 cartridge holder
106 needle assembly
108 inner needle cap
110 outer needle cap
112 protective cap
114 dose dial
116 dosage window
120 injection button
122 cartridge
124 barrel
126 piston
128 seal
130 piston rod
132 pressure piece
140 dose indicator
150 drive sleeve
212 elongated member
212a,b,c,d,e section
214 coating
216 thread

The invention claimed is:

1. A sensor arrangement for an injection device, the sensor arrangement comprising:
    an elongated member arrangeable inside a housing of the injection device such that the elongated member extends in an axial direction relative to the housing, the elongated member having at least a first section of a first magnetization and a second section of a second magnetization, wherein a direction of the first magnetization differs from a direction of the second magnetization, and wherein the first section and the second section are separated in the axial direction; and
    at least one magnetic sensor attachable to the housing to detect an axial position of at least one of the first section and the second section of the elongated member;
    wherein the elongated member is mechanically engaged with a device component that is axially displaceable along the elongated member and relative to the housing of the injection device, and wherein the device component is configured to attenuate or to amplify a magnetic field of the elongated member.

2. The sensor arrangement according to claim 1, wherein the first section and the second section are separated in the axial direction in a non-overlapping manner.

3. The sensor arrangement according to claim 1, wherein the elongated member comprises a helical pattern of differently magnetized sections.

4. The sensor arrangement according to claim 1, wherein the elongated member comprises a third section of a third magnetization and a fourth section with a fourth magnetization, wherein the second section is located axially between the first section and the third section, and wherein the third section is located axially between the second section and the fourth section.

5. The sensor arrangement according to claim 4, wherein the direction of the first magnetization is opposite to a direction of the third magnetization, wherein the direction of the second magnetization is opposite to a direction of the fourth magnetization, and wherein the direction of the first magnetization extends at a predefined non- zero angle with regard to the direction of the second magnetization.

6. The sensor arrangement according to claim 1, wherein the at least one magnetic sensor is arranged in a sensor housing attachable to the housing of the injection device.

7. The sensor arrangement according to claim 1, comprising a magnetic sensor array having multiple sensor elements separated from each other in the axial direction, the at least one magnetic sensor being one or more of the multiple sensor elements.

8. The sensor arrangement according to claim 1, wherein the elongated member comprises a magnetized coating.

9. The sensor arrangement according to claim 1, wherein the device component is ferromagnetic or ferrimagnetic.

10. The sensor arrangement according to claim 1, wherein the device component is permanently magnetized.

11. The sensor arrangement according to claim 1, wherein the device component magnetically interacts with the elongated member.

12. The sensor arrangement according to claim 1, wherein the device component is threadedly engaged with the elongated member, and is rotatably fixed to the housing but is slidably displaceable relative to the housing.

13. The sensor arrangement according to claim 1, wherein the device component is threadedly engaged with the housing and is rotatably fixed to the elongated member but is slidably displaceable relative to the elongated member.

14. The sensor arrangement according to claim 1, wherein the device component is a last dose limiting member of a drive mechanism of the injection device, wherein the last dose limiting member prevents setting a dose on the injection device that exceeds an amount of medicament left in a cartridge of the injection device.

15. The sensor arrangement according to claim 1, wherein the sensor arrangement is part of a drive mechanism of the injection device, and wherein the elongated member is a piston rod, a dose indicator, or a drive sleeve of the drive mechanism.

16. An injection device for setting and injecting of a dose of a liquid medicament, comprising:
   a housing to accommodate a cartridge filled with the liquid medicament;
   a drive mechanism comprising a piston rod to operably engage with a piston of the cartridge; and
   a sensor arrangement attached to the housing or arranged inside the housing, the sensor arrangement comprising:
      an elongated member located inside the housing, extending in an axial direction and having at least a first section and a second section, the first section having a different magnetization than the second section, the first section and the second section being separated in the axial direction, and
      at least one magnetic sensor element attached to the housing to detect an axial position of at least one of the first section and the second section of the elongated member; and
   wherein the elongated member is mechanically engaged with a device component that is axially displaceable along the elongated member and relative to the housing of the injection device and wherein the device component is configured to attenuate or to amplify a magnetic field of the elongated member.

17. The injection device according to claim 16, wherein the elongated member is mechanically engaged with a device component that is axially displaceable along the elongated member, wherein the device component is threadedly engaged with the elongated member, and is rotatably fixed to the housing but is slidably displaceable relative to the housing.

18. The injection device according to claim 16, further comprising the cartridge filled with the liquid medicament.

19. A sensor arrangement for an injection device, the sensor arrangement comprising:
   an elongated member arrangeable inside a housing of the injection device such that the elongated member extends in an axial direction relative to the housing, the elongated member having at least a first section of a first magnetization and a second section of a second magnetization, wherein a direction of the first magnetization differs from a direction of the second magnetization, and wherein the first section and the second section are separated in the axial direction; and
   wherein the elongated member comprises a third section of a third magnetization and a fourth section with a fourth magnetization, wherein the second section is located axially between the first section and the third section, and wherein the third section is located axially between the second section and the fourth section and wherein the direction of the first magnetization is opposite to a direction of the third magnetization and wherein the direction of the second magnetization is opposite to a direction of the fourth magnetization, wherein the directions of the first magnetization, the second magnetization, the third magnetization and the fourth magnetization extend at predefined non-zero angles with regard to each other.

* * * * *